| United States Patent [19] | [11] Patent Number: 4,658,826 |
| --- | --- |
| Weaver | [45] Date of Patent: Apr. 21, 1987 |

[54] SKIN PREPARATORY COMPOSITION FOR USE WITH ELECTROCARDIOGRAPH AND ELECTROENCEPHALOGRAPH MONITORING ELECTRODES

[75] Inventor: David O. Weaver, Denver, Colo.

[73] Assignee: D. O. Weaver and Company, Aurora, Colo.

[21] Appl. No.: 171,101

[22] Filed: Jul. 22, 1980

Related U.S. Application Data

[63] Continuation-in-part of Ser. No. 11,312, Feb. 12, 1979, abandoned.

[51] Int. Cl.$^4$ ............................ A61B 5/04; H01B 1/06
[52] U.S. Cl. ..................................... 128/640; 128/802; 128/803; 252/315.3; 252/518; 252/DIG. 5
[58] Field of Search ................. 252/316, 521, DIG. 5, 252/315.3, 518; 128/803, 419 R, 640, 802

[56] References Cited

U.S. PATENT DOCUMENTS

| | | | |
| --- | --- | --- | --- |
| 2,064,725 | 12/1936 | Blech | 252/DIG. 5 |
| 2,943,021 | 6/1960 | Landberg | 424/230 X |
| 3,567,657 | 3/1971 | Lichtenstein | 252/500 |
| 3,989,050 | 11/1976 | Buchalter | 128/419 R |

*Primary Examiner*—Richard D. Lovering
*Attorney, Agent, or Firm*—Jack E. Ebel

[57] ABSTRACT

A skin preparatory composition for use in conjunction with electrocardiograph and electroencephalograph monitoring electrodes containing karaya gum in an amount sufficient to adhere the electrodes to the skin, sodium citrate in an amount which imparts sufficient electrolytic properties to the composition, an abrasive in an amount effective to reduce the impedance of the skin to a satisfactory level when the composition is applied thereto, and a vehicle for these constituents. The karaya gum effectively removes any perspiration, dirt, natural body oils, moisturing oils and lotions, and the attendant electrical interference from the skin. A wetting agent in an amount sufficient to aid in solubilizing the karaya gum in the vehicle and a preservative in an amount sufficient to extend the useful life of the composition may also be incorporated in the composition.

11 Claims, No Drawings

SKIN PREPARATORY COMPOSITION FOR USE WITH ELECTROCARDIOGRAPH AND ELECTROENCEPHALOGRAPH MONITORING ELECTRODES

This is a continuation-in-part of application Ser. No. 011,312, filed Feb. 12, 1979, and now abandoned.

BACKGROUND OF THE INVENTION

This invention relates to a skin preparatory composition, and more particularly, to such a composition utilized in conjunction with electrocardiograph or electroencephalograph monitoring electrodes.

An electrocardiograph (ECG or EKG) is an instrument utilized to record changes in electrical potential which occur during the heartbeat. An electrocardiograph is especially useful in diagnosing abnormal cardiac rhythm and myocardial damage. An electroencephalographe (EEG) is an apparatus for detecting and recording electrical brain waves for subsequent medical diagnosis and prognosis. Both the electrocardiograph and electroencephalograph utilize monitoring electrodes which are attached to the patient's skin so as to transmit electrical waves generated by the heart and brain, respectively, to a recorder. For example, evoked potential equipment can be employed in conjunction with EEG electrodes to monitor electrical brain wave activity, whereas a holter monitoring device can be employed in conjunction with EKG electrodes to record electrical activity of the heart during a patient's daily activities. The EKG electrode is generally a relatively large circular disc constructed of a conductive material, while the EEG electrode is a relatively smaller disc which is conventionally attached to the scalp by means of a bentonite clay paste which is allowed to harden. In particular, the EKG electrode is employed in stress tests where the patient is subjected to intense periods of exercise such as on a treadmill so as to stimulate the heart and aid in identifying heart rhythm anomalies. The EKG electrode is also employed in conjunction with a holter monitoring device which monitors a patient's electrical heart waves generated during normal activity. Thus, the EKG electrode is subject to movement of the skin to which it is attached, and hence, is prone to slide on the patient's skin thereby hindering accurate EKG readings or to become completely disattached from the patient's skin. It is imperative that the EKG electrode be held stationary on the patient's body as any movement at the point of connection thereto will create electrical interference, i.e., electrical readings from sources other than the cardiac system, for example, from muscle movements. In an attempt to overcome this problem, EKG electrodes have been constructed with a gel positioned centrally on the outer face thereof which contacts the skin and an annular sealant ring surrounding the gel and concentric with the outer face. The annular sealant ring serves to adhere the electrode to the patient's skin, while the gel is formulated to include an electrolyte so as to aid in transmitting electrical waves. Sodium citrate is an example of an electrolyte which has been previously employed in conventional gels. These gels usually employ carboxymethylcellulose as a base and do not contain an adhesive constituent. The annular sealant ring is solely relied upon to adhere the electrode to the patient's skin. These conventional electrodes have not successfully adhered to a patient's skin during stress tests.

Another problem which has plagued the effectiveness of both EKG and EEG electodes is the artifact created by the outermost, dried out layer of skin, the epidermus corneum. This layer of skin acts as an insulator to electrical current produced by the brain and heart thereby preventing an accurate reading of the actual brain or heart electrical current. Thus, to obtain an accurate reading it has been necessary to abrade the epidermus corneum to reduce the resistance of a patient's skin to a satisfactory level. This abrading technique is especially relevant with respect to EEG electrodes as the extremely small voltage generated by the brain requires a very sensitive reading. Conventional techniques for abrading include scrapping the skin with a hypodermic needle, removing the epidermus corneum with emory boards or solvents, such as, acetone or alcohols, and utilizing a battery operated drill equipped with a burring tool to abrade the skin. However, such abrading techniques are irritable to the patient, pose safety problems, and do not always provide satisfactory reduced skin resistance levels.

The effectiveness of both EKG and EEG electrodes is still further reduced by perspiration, dirt, natural body oils, and moisturizing oils and lotions, each of which creates interference to electrical conductivity as well as impedes secure electrode attachments to the skin. Such problems are not alleviated by application of any of the conventional techniques previously described.

Thus it can be appreciated that a need exists for a skin preparatory composition for use with EEG and EKG electrodes which improves the adhesiveness of the electrode to skin while reducing the resistance of the skin to a satisfactory level and effectively removes any perspiration, dirt, natural body oils, and moisturizing oils and lotions.

Accordingly, it is an object of the present invention to provide a skin preparatory composition which reduces the resistance of skin to a satisfactory level for both EEG and EKG monitoring electrodes.

It is another object of the present invention to provide a skin preparatory composition which improves the adhesion of an EKG monitoring electrode to a patient's skin, particularly during stress testing. It is a further object of the present invention to provide a skin preparatory composition which effectively removes perspiration, dirt, natural body oils, and moisturizing oils and lotions from a patient's skin and the electrical interference associated therewith.

These and other objects and advantages of the invention will be apparent from the following detailed description.

BRIEF SUMMARY OF THE INVENTION

The present invention relates to a skin preparatory composition for use with electrocardiograph and electroencephalograph diagnostic electrodes. When applied to skin, the composition functions to provide for improved adhesion between the electrode and the skin to reduce the impedance of skin to a satisfactory level for use in conjunction with an electrocardiograph or electroencephalograph, and also to effectively reduce the concentration of any perspiration, dirt, natural body oil, moisturizing oil, or moisturizing lotion present on skin. The composition consists essentially of karaya gum in an amount between about 1 wt % and about 15 wt %, sodium citrate in an amount between about 1.5 wt % and about 30 wt %, an abrasive in an amount between about 5 wt % and about 40 wt % and a suitable liquid vehicle for these constituents in an amount between about 35 wt % and 85 wt %. The composition may also include a wetting agent in an amount sufficient to aid in solubilizing the karaya gum in the vehicle and a preservative in an amount sufficient to extend the useful life of the composition.

DETAILED DESCRIPTION

The skin preparatory composition of the present invention contains karaya gum, sodium citrate, an abrasive and a suitable liquid vehicle for these constituents. Other constituents which do not detract from the abrasive and adhesive properties of the composition of the present invention may be added thereto as necessary, such as a wetting agent to aid in solubilizing karaya in the vehicle and a preservative to extend the useful life of the composition. Karaya gum serves as an adhesive in the composition of the present invention. As defined by ninth edition of "The Condensed Chemical Dictionary" 1977, karaya gum is a hydrophilic gum which exudes from certain Indian trees of the genus Sterculia. Karaya gum may also be termed sterculia gum, Indian tragacanth, kodaya gum and goma caraia. Any commercially available source of karaya gum may be suitable for use in the present invention.

In addition, it has been unexpectedly discovered that karaya gum as utilized in the present invention effectively removes perspiration, dirt, natural body oils, and moisturizing oils and lotions from the skin. While is is not completely understood exactly why karaya gum employed in accordance with the present invention results in such removal, it is believed that karaya gum emulsifies or solubilizes perspiration, dirt, natural body oils, and moisturizing oils and lotions from the skin.

Sodium citrate functions as an electrolyte in the composition of the present invention and may be added in either crystalline or granular form. Any commercially available reagant grade or USP grade sodium citrate may be utilized.

Any suitable abrasive, such as pumice, quartz crystals or polyvinyl chloride, may be employed in the composition of the present invention, although it is preferred to employ pumice. Pumice is a highly porous igneous rock containing complex silicates of aluminum, potassium and sodium. Pumice is soluble in water and is not attacked by acids or alkali hydroxide solutions. Pumice is employed as fine pumice which is defined by the "National Formulary XIII" as being of a size such that not less than 95% passes through a No. 150 standard mesh sieve, and not more than 75% passes through a No. 200 standard mesh sieve.

An aqueous vehicle is utilized in the composition of the present invention and may include thickeners, such as, carboxymethylcellulose, to achieve a desired consistency, and skin moisturizing agents, such as, glycerin. When a wetting agent is utilized to aid in solubilizing karaya gum, it is preferred to utilize glycerin. And when preservatives are incorporated into the skin preparatory composition, it is preferred to utilize a combination of two or more esters of para-hydroxybenzoic acid. In particular, it is preferred to utilize a combination of methylhydroxybenzoate (Methylparaben USP) and propylhydroxybenzoate (Propylparaben USP).

The constituents of the skin preparatory composition of the present invention may be employed within the following guidelines and ranges of wt %. As employed herein, the term "wt %" is defined as the percentage ratio of the weight of any particular constituent employed in the composition of the present invention to the total weight of the composition of the present invention. Sodium citrate is employed in an amount sufficient to impart adequate electrical conductivity to the composition but less than an amount which would cause extreme irritation to the patient's skin. As such, sodium citrate may be employed in an amount of from about 1.5 wt % to about 30 wt %. Karaya is employed in an amount which is sufficient to suspend the abrasive within the composition of the present invention, but in an amount less than that which would render the composition too viscous for the intended use. Therefore, karaya may be employed in an amount of from about 5 wt % to about 40 wt %. The abrasive, e.g. fine pumice, of the composition of the present invention is employed in an amount sufficient to abrade the epidermus corneum, and as such, may be employed in an amount from about 5 wt % to about 40 wt %. The vehicle, i.e. water, may be utilized in the composition in such an amount as well maintain the composition as a dispersion having a gel-like consistency. Thus, the vehicle may be employed in amounts from about 35 wt % to about 85 wt %.

Further, the wetting agent, e.g. glycerin, may be employed in any amount when necessary to aid the solubilization of karaya in the vehicle. And the preservative may be utilized in that amount recommended for use in conjunction with pharmaceuticals.

Thus, it will be appreciated that if certain characteristics of the skin preparatory composition are desired, such characteristics will dictate the constituency concentrations of the composition. For example, it way be desirable to formulate a composition for use in conjunction with EEG electrodes which contains a relatively high concentration of sodium citrate, e.g. 25 wt %, so as to provide for a highly electrolytic composition. As such, karaya and the abrasive may be incorporated into the composition in relatively low concentrations within the ranges aforedescribed and still provide requisite abrasion and adhesion for the composition. As another example, if relatively high degree of abrasion is desired, karaya must be employed in a relatively high concentration to suspend the abrasive within the composition, but sodium citrate may be utilized in any amount within the aforedescribed range which will impart adequate electrolytic properties to the composition of the present invention. Lastly, it may be desirable to formulate the skin preparatory composition with relatively high concentrations of all constituents thereof except the vehicle. Subsequently, the composition may be diluted upon the addition of a suitable vehicle, e.g. water, so as to obtain the desired consistency and characteristics.

The preferred skin preparatory composition of the present invention is about 6.5 wt % of sodium citrate, about 2.7 wt % of karaya gum, about 4.0 wt % of glycerin, about 21.6 wt % of fine pumice, about 0.18 wt % of methylhydroxybenzoate, about 0.02 wt % of propylhydroxybenzoate and about 65.0 wt % of water.

EXAMPLE 1

The following example is illustrative of the preferred manner of making the skin preparatory composition of the present invention.

Water at ambient temperature and in an amount of 27.9 gallons (105,600 ml) was poured into a 40 gallon stainless steel container. Methylparaben in an amount of 262 grams, propylparaben in an amount of 29 grams and sodium citrate USP in an amount of 19.2 lbs (8736 grams) were added to the water. The contents of the container were then stirred utilizing a conventional power mixer. Next, glycerin in the amount of 4950 grams was measured into a Hobart blender. With the blender operating, 3349 grams of karaya gum were slowly added thereto. The resultant mixture was completely incorporated. Immediately, this karaya-glycerin mixture was slowly added to the container mixture while the blender was operating until incorporation was complete. Again with the blender operating, 58.7 lbs of fine pumice was added to the container mixture and blended until incorporation was complete. This procedure resulted in 30 gallons (3840 oz) of the skin preparatory composition.

The skin preparatory composition of the present invention may be applied in the following manners. For ECG or EKG electrodes, the skin preparatory composition is rubbed onto the skin at the entire electrode site area with a suitable applicator, such as a dry gauze pad, for 5 or 10 seconds. Any excess composition may be wiped away and the electrode is applied to the skin. In some instances, electrode adhesiveness may be enhanced by excess composition, and therefore, it may not be necessary to wipe the excess away from the electrode site. Further, certain electrode adhesives, such as the clear plastic variety, may function more effectively without contacting the skin preparatory composition. Thus, the composition may be applied only to the actual point of conduction. For long term stress testing, it is desirable to remove the excess composition to reduce any potential skin irritation due to residual electrolytes.

For EEG electrodes, the skin preparatory composition is rubbed onto the electrode site with a suitable applicator, such as a cotton swab, and allowed to dry. Thereafter, the electrode and adhesive are applied to the site. The composition should be applied sparingly and allowed to dry to prevent movement of the EEG electrode.

It should be noted that the skin preparatory composition is not intended for use as an electrode gel. Therefore, the composition of the present invention should not be utilized in conjunction with current inducing electrodes, such as, defibrillator or neurostimulating equipment.

Thus, when utilized in conjunction with ECG or EKG diagnostic electrodes, the skin preparatory composition of the present invention provided improved adhesiveness over stress testing periods (72 hours tests) without excessive skin irritation. Also, by utilizing the preparatory skin composition of the present invention, skin impedance may be reduced to about 1000 ohms. It is desired to reduce the impedance to below 5000 ohms to obtain satisfactory results.

While various embodiments and modifications of this invention have been described in the foregoing description, further modifications will be apparent to those skilled in the art. Such modifications are included within the scope of this invention as defined by the following claims.

I claim:

1. A skin preparatory composition for use with electrocardiograph and electroencephalograph monitoring electrodes, the composition functioning to suitably adhere the electrodes to the skin, to abrade the skin to reduce the impedance thereof to a satisfactory level for use in conjunction with an electrocardiograph or electroencephalograph, and to effectively remove perspiration, dirt, natural body oils, and moisturizing oils and lotions from the skin, the composition consisting essentially of:
   karaya gum in an amount between about 1 wt % and about 15 wt % so as to adhere the electrodes to the skin and to remove said perspiration, dirt, natural body oils, and moisturizing oils and lotions from the skin;
   sodium citrate in an amount between about 1.5 wt % and about 30 wt % so as to impart sufficient electrolytic properties to said composition thereby rendering said composition useful with said electrodes;
   an abrasive in an amount between about 5 wt % and about 40 wt % effective to reduce the impedance of said skin to said satisfactory level when said composition is applied thereto; and
   an aqueous vehicle in an amount between about 35 wt % and about 85 wt %.

2. The composition of claim 1 wherein said abrasive is fine pumice.

3. The composition of claim 1 wherein said composition further consists essentially of:
   a wetting agent in an amount sufficient to aid in solubilizing the karaya gum in said vehicle.

4. The composition of claim 3 wherein said wetting agent is glycerin.

5. The composition of claim 3 wherein said composition further consists essentially of:
   a combination of methylhydroxybenzoate in an amount of about 0.18 wt % and propylhydroxybenzoate in an amount of about 0.02 wt %, said combination functioning as a preservative to extend the useful life of said composition.

6. The composition of claim 1 wherein said composition further consists essentially of:
   a preservative in an amount sufficient to extend the useful life of said composition.

7. The composition of claim 6 wherein said preservative is a combination of methylhydroxybenzoate in an amount of about 0.18 wt % and propylhydroxybenzoate in an amount of about 0.02 wt %.

8. The composition of claim 1 wherein said composition further consists essentially of:
   a thickening agent in an amount sufficient to impart a desired consistency to said composition.

9. The composition of claim 8 wherein said thickening agent is carboxymethylcellulose.

10. A preparatory skin composition for use with electrocardiograph and electroencephalograph monitoring electrodes, the composition consisting of:
    sodium citrate in an amount of about 6.5 wt %;
    karaya gum in an amount of about 2.7 wt %;
    glycerin in an amount of about 4.0 wt %;
    fine pumice in an amount of about 21.6 wt %;
    methylhydroxybenzoate in an amount of about 0.18 wt %;
    propylhydroxybenzoate in an amount of about 0.02 wt %; and
    water in an amount of about 65 wt %.

11. A process for securing a monitoring electrode to a patient's skin, said process comprising:
    (a) contacting said skin with a composition consisting essentially of:
        sodium citrate in an amount of aoout 6.5 wt %;
        karaya gum in an amount of about 2.7 wt %;
        glycerin in an amount of about 4.0 wt %;
        fine pumice in an amount of about 21.6 wt %;

methylhydroxybenzoate in an amount of about 0.18 wt %;
propylhydroxybenzoate in an amount of about 0.02 wt %; and
water in an amount of about 65 wt %; and thereafter,
(b) applying said monitoring electrode to said skin, said composition firmly adhering said electrode to said skin while reducing the electrical resistance of said skin to a satisfactory level and effectively removing any perspiration, dirt, natural body oils, and moisturizing oils and lotions from said skin.

* * * * *